United States Patent
Hall et al.

(10) Patent No.: US 11,366,113 B2
(45) Date of Patent: Jun. 21, 2022

(54) METHODS FOR IDENTIFYING PATTERNS OF IFN INDUCED EXPRESSION AND USE IN DIAGNOSIS, MONITORING AND THERAPY

(71) Applicant: THE JOHNS HOPKINS UNIVERSITY, Baltimore, MD (US)

(72) Inventors: John Clayton Hall, Baltimore, MD (US); Livia Casciola-Rosen, Baltimore, MD (US); Antony Rosen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/973,688

(22) Filed: May 8, 2018

(65) Prior Publication Data
US 2018/0259518 A1    Sep. 13, 2018

Related U.S. Application Data

(62) Division of application No. 14/401,655, filed as application No. PCT/US2013/040843 on May 14, 2013, now abandoned.

(60) Provisional application No. 61/648,251, filed on May 17, 2012.

(51) Int. Cl.
*G01N 33/564* (2006.01)
*G01N 33/68* (2006.01)
*C12Q 1/6886* (2018.01)

(52) U.S. Cl.
CPC ......... *G01N 33/564* (2013.01); *C12Q 1/6886* (2013.01); *G01N 33/6842* (2013.01); *G01N 33/6866* (2013.01); *G01N 33/6893* (2013.01); *C12Q 2600/106* (2013.01); *C12Q 2600/158* (2013.01); *G01N 2800/102* (2013.01)

(58) Field of Classification Search
CPC ........... G01N 33/564; G01N 2800/102; C12Q 2600/106; C12Q 2600/158
See application file for complete search history.

(56) References Cited

U.S. PATENT DOCUMENTS

| | | | |
|---|---|---|---|
| 4,391,904 A | 7/1983 | Litman et al. | |
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,150,584 A | 11/2000 | Kucherlapati et al. | |
| 2006/0018875 A1* | 1/2006 | Blatt | A61K 38/21 424/85.6 |
| 2008/0261226 A1 | 10/2008 | Wang et al. | |
| 2010/0143372 A1 | 6/2010 | Yao et al. | |

FOREIGN PATENT DOCUMENTS

EP    2151504 A1    2/2010

OTHER PUBLICATIONS

Chen et al. The Journal of Cell Biology. 2000. 151 (6):1321. (Year: 2000).*
Raju et al. Brain. 2005. 128:1887. (Year: 2005).*
Zhou et al. Med Sci Monit. 2004. 10(7):BR191-197. (Year: 2004).*
Hall et al. PNAS. 2012. 109(43):17609. (Year: 2012).*
Yao et al. Arthritis Research & Therapy. 2010. 12(Suppl 1):S6. (Year: 2010).*
Baechler et al. Immunological Reviews. 2006. 2010:120. (Year: 2006).*
Banchereau et al. Immunity. 2006. 25:383. (Year: 2006).*
Tezak et al. The Journal of Immunology. 2002. 168:4154. (Year: 2002).*
Affymetrix Probe Information. Retrieved on Feb. 3, 2021 from online:http://www.affymetrix.com/analysis/netaffx/xmlquery.affx?netaffx=netaffx4_annot (Year: 2021).*
Affymetrix Probe Information 2.0. Retrieved on Aug. 16, 2021 from online:http://www.affymetrix.com/analysis/netaffx/xmlquery.affx?netaffx=netaffx4_annot. (Year: 2021).*
Marioni et al. Genome Res. 2008. 18:1509-1517. (Year: 2008).*
Hjelmervik, et al., Gene expression profiling of minor salivary glands clearly distinguishes primary Sjögren's syndrome patients from healthy control subjects. Arthritis Rheum. May 2005;52(5):1534-44.
Gottenberg, et al., Activation of IFN pathways and plasmacytoid dendritic cell recruitment in target organs of primary Sjögren's syndrome. Proc Natl Acad Sci U S A. Feb. 21, 2006;103(8):2770-5.
Wildenberg, et al., Systemic increase in type I interferon activity in Sjogren's syndrome: a putative role for plasmacytoid dendritic cells. Eur J Immunol. Jul. 2008;38(7):2024-33.
Emamian, et al., Peripheral blood gene expression profiling in Sjögren's syndrome. Genes Immun. Jun. 2009;10(4):285-96.
Bave, et al., Activation of the type I interferon system in primary Sjögren's syndrome: a possible etiopathogenic mechanism. Arthritis Rheum Apr. 2005;52(4):1185-95.
Greenberg, et al., Interferon-alpha/beta-mediated innate immune mechanisms in dermatomyositis. Ann Neurol. May 2005;57(5):664-78.

(Continued)

*Primary Examiner* — Joseph G. Dauner
(74) *Attorney, Agent, or Firm* — Fish & Richardson P.C.

(57) ABSTRACT

The present inventors identified a subpopulation of genes induced by type I and type II IFNs in a human submandibular gland (HSG) epithelial cell line. Unexpectedly, it was found that the majority of genes that are highly up-regulated by IFN-α are also highly induced by IFN-γ. In contrast, there was a substantial group of genes that are highly induced by IFN-γ only. In target tissues, this identified subpopulation of genes and probes allow different IFN patterns to be discerned, enabling more precise molecular classification of patient subpopulations. The identified gene probes are useful for selecting and monitoring therapy, and for defining efficacy of novel agents in the autoimmune rheumatic diseases.

9 Claims, 7 Drawing Sheets

(56) References Cited

OTHER PUBLICATIONS

Walsh, et al., Type I interferon-inducible gene expression in blood is present and reflects disease activity in dermatomyositis and polymyositis. Arthritis Rheum. Nov. 2007;56(11):3784-92.
Tan, et al., Signatures of differentially regulated interferon gene expression and vasculotrophism in the peripheral blood cells of systemic sclerosis patients. Rheumatology (Oxford) Jun. 2006;45(6):694-702.
Baechler, et al., Interferon-inducible gene expression signature in peripheral blood cells of patients with severe upus. Proc Natl Acad Sci U S A. Mar. 4, 2003;100(5):2610-5.
Bennett, et al., Interferon and granulopoiesis signatures in systemic lupus erythematosus blood. J Exp Med. Mar. 17, 2003;197(6):711-23.
Han, et al., Analysis of gene expression profiles in human systemic lupus erythematosus using oligonucleotide microarray Genes Immun. Apr. 2003;4(3):177-86.
Corless, et al., Molecular pathobiology of gastrointestinal stromal sarcomas. Annu Rev Pathol. 2008;3:557-86.
Bertos, et al., Breast cancer—one term, many entities? J Clin Invest. Oct. 3, 2011; 121(10): 3789-3796.
Hooks, et al., Immune interferon in the circulation of patients with autoimmune disease. N Engl J Med. Jul. 5, 1979;301(1):5-8.
Bissonnette, et al., A randomized, double-blind, placebo-controlled, phase I study of MEDI-545, an anti-interferon-alfa monoclonal antibody, in subjects with chronic psoriasis. J Am Acad Dermatol. Mar. 2010;62(3):427-36.
Grassi, et al., Identification of granzyme B-expressing CD-8-positive T cells in lymphocytic inflammatory infiltrate in cutaneous lupus erythematosus and in dermatomyositis. Clin Exp Dermatol. Dec. 2009,34(8):910-4.
Christodoulou, et al., Characteristics of the minor salivary gland infiltrates in Sjögren's syndrome. J Autoimmun. Jun. 2010;34(4):400-7.
Mammen, et al., Expression of the dermatomyositis autoantigen Mi-2 in regenerating muscle. Arthritis Rheum. Dec. 2009;60(12):3784-93.
Negishi, et al., A critical link between Toll-like receptor 3 and type II interferon signaling pathways in antiviral innate immunity. Proc Natl Acad Sci U S A Dec. 23, 2008;105(51):20446-51.
Bave, et al., The combination of apoptotic U937 cells and lupus IgG is a potent IFN-alpha inducer. J Immunol. Sep. 15, 2000;165(6):3519-26.
Lau, et al., RNA-associated autoantigens activate B cells by combined B cell antigen receptor/Toll-like receptor 7 engagement. J Exp Med. Nov. 7, 2005; 202(9): 1171-1177.
Tsunawaki, et al., Possible function of salivary gland epithelial cells as nonprofessional antigen-presenting cells in the development of Sjögren's syndrome. J Rheumatol. Sep. 2002;29(9):1884-96.
Kulkarni, et al., Interferon-gamma sensitizes the human salivary gland cell line, HSG, to tumor necrosis factor-alpha induced activation of dual apoptotic pathways Apoptosis. Dec. 2006;11(12):2205-15.
Ittah, et al., B cell-activating factor of the tumor necrosis factor family (BAFF) is expressed under stimulation by interferon in salivary gland epithelial cells in primary Sjögren's syndrome. Arthritis Res Ther. 2006;8(2):R51.
Wu, et al., Interferon-gamma induced cell death in a cultured human salivary gland cell line. J Cell Physiol. May 1996;167(2):297-304.
Meehan, et al., Interferon-gamma induces a decrease in the intracellular calcium pump in a human salivary gland cell line. Am J Physiol. Dec. 1997;273(6 Pt 1):C2030-6.
Baker, et al., Proinflammatory cytokines tumor necrosis factor-alpha and interferon-gamma alter tight junction structure and function in the rat parotid gland Par-C10 cell line. Am J Physiol Cell Physiol. Nov. 2008;295(5):C1191-201.
Benjamini, et al., Controlling the False Discovery Rate: A Practical and Powerful Approach to Multiple Testing. J R Stat Soc. 1995;57(1):289-300.

Reich, et al., GenePattern 2.0. Nat Genet. May 2006;38(5):500-1.
Van Der Pouw Kraan, et al., Rheumatoid arthritis subtypes identified by genomic profiling of peripheral blood cells: assignment of a type I interferon signature in a subpopulation of patients. Ann Rheum Dis. Aug. 2007;66(8):1008-14.
Pascual, et al., How the study of children with rheumatic diseases identified interferon-alpha and interleukin-1 as novel therapeutic targets. Immunol Rev. Jun. 2008;223:39-59.
Gottenberg, et al., "Activation of IFN pathways and plasmacytoid dendritic cell recruitment in target organs of primary Sjogren's syndrome", PNAS, Feb. 13, 2006, vol. 103, No. 8, pp. 2770-2775.
Briken, et al., "Interferon regulatory factor 1 is required for mouse Gbp gene activation by gamma interferon", Molecular and Cellular Biology, Feb. 1995, vol. 15, No. 2, pp. 975-982.
Hjelmervik, et al., "Gene expression profiling of minor salivary glands clearly distinguishes primary Sjogren's syndrome patients from healthy control subjects", Arthritis & Rheumatism, May 2005, vol. 52, No. 5, pp. 1534-1544.
Li, Q.Z., et al., "Interferon signature gene expression is correlated with autoantibody profiles in patients with incomplete lupus syndromes", Clinical and Experimental Immunology, vol. 159, No. 3, Mar. 1, 2010, pp. 281-291.
Hall, J.C., et al., "Precise probes of type II interferon activity define the origin of interferon signatures in target tissues in rheumatic diseases" Proceedings of the National Academy of Sciences USA, vol. 109, No. 43, Oct. 8, 2012 pp. 17609-17614.
Extended European search report, dated Dec. 11, 2015, for EP application EP13791530.
Kylaniema, M., et al., "Gene expression signatures characterizing the development of lymphocyte response during experimental Chlamydia pneumoniae infection" Microbial Pathogenesis 46 (2009) 235-242.
International Search Report and Written Opinion dated Aug. 20, 2013 for PCT/US2013/040843.
Bohan et al., "Polymyositis and dermatomyositis (first of two parts)," N Engl J Med, Feb. 13, 1975, 292(7):344-347.
Bohan et al., "Polymyositis and dermatomyositis (second of two parts)," N Engl J Med, 1975, 292(8):403-407.
Casciola-Rosen et al., "Enhanced autoantigen expression in regenerating muscle cells in idiopathic inflammatory myopathy," J Exp Med., 2005, 201(4):591-601.
Eisen et al., "Cluster analysis and display of genome-wide expression patterns," Proceedings of the National Academy of Sciences, Dec. 8, 1998, 95(25): 8 Pages.
Monroe D. "Liposome immunoassay: a new ultrasensitive analytical method," Am. Clin. Prod. Rev., 1986 5:34-41.
Neuberger M., "Generating high-avidity human mabs in mice," Nature Biotechnology, 1996, 14:826.
Kostelny, et al., Formation of a bispecific antibody by the use of leucine zippers. J Immunol. Mar. 1, 1992;148(5):1547-53.
Pack, et al. Miniantibodies: use of amphipathic helices to produce functional, flexibly linked dimeric FV fragments with high avidity in *Escherichia coli*. Biochemistry. Feb. 18, 1992;31(6):1579-84.
Gruber, et al., Efficient tumor cell lysis mediated by a bispecific single chain antibody expressed in *Escherichia coli*. J Immunol. Jun. 1, 1994;152(11):5368-74.
Zhu, et al., Remodeling domain interfaces to enhance heterodimer formation. Protein Sci. Apr. 1997; 6(4): 781-788.
Hu, et al., Minibody: A novel engineered anti-carcinoembryonic antigen antibody fragment (single-chain Fv-CH3) which exhibits rapid, high-level targeting of xenografts. Cancer Res. Jul. 1, 1996;56(13):3055-61.
Adams, et al., Highly specific in vivo tumor targeting by monovalent and divalent forms of 741F8 anti-c-erbB-2 single-chain Fv. Cancer Res. Sep. 1, 1993;53(17):4026-34.
McCartney, et al., Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides. Protein Eng. Mar. 1995;8(3):301-14.
Huse, et al., Generation of a large combinatorial library of the immunoglobulin repertoire in phage lambda. Science. Dec. 8, 1989;246(4935):1275-81.

(56) References Cited

OTHER PUBLICATIONS

Ward, et al., Binding activities of a repertoire of single immunoglobulin variable domains secreted from *Escherichia coli*. Nature. Oct. 12, 1989;341(6242):544-6.

Vaughan, et al., Human antibodies with sub-nanomolar affinities isolated from a large non-immunized phage display library. Nat Biotechnol. Mar. 1996;14(3):309-14.

Jones, et al., Replacing the complementarity-determining regions in a human antibody with those from a mouse. Nature. May 29-Jun. 4, 1986;321(6069):522-5.

Riechmann, et al., Reshaping human antibodies for therapy. Nature. Mar. 24, 1988;332(6162):323-7.

Presta, Antibody engineering. Curr Op Struct Biol. Aug. 1992;2(4):593-596.

Verhoeyen, et al., Reshaping human antibodies: grafting an antilysozyme activity. Science. Mar. 1988;239(4847):1534-1536.

McCafferty, et al., Phage antibodies: filamentous phage displaying antibody variable domains. Nature. Dec. 6, 1990;348(6301):552-4.

Hoogenboom, et al., By-passing immunisation. Human antibodies from synthetic repertoires of germline VH gene segments rearranged in vitro. J Mol Biol. Sep. 20, 1992;227(2):381-8.

Marks, et al., By-passing immunization. Human antibodies from V-gene libraries displayed on phage. J Mol Biol. Dec. 5, 1991;222(3):581-97.

Boder, et al., Yeast surface display for screening combinatorial polypeptide libraries. Nat Biotechnol. Jun. 1997;15(6):553-7.

Hanes, et al., In vitro selection and evolution of functional proteins by using ribosome display. Proc Natl Acad Sci U S A. May 13, 1997;94(10):4937-42.

Jakobavits, Production and selection of antigen-specific fully human monoclonal antibodies from mice engineered with human Ig loci. Adv Drug Deliv Rev. Apr. 6, 1998;31(1-2):33-42.

Marks, et al., By-passing immunization: building high affinity human antibodies by chain shuffling. Biotechnology (N Y). Jul. 1992;10(7):779-83.

Lonberg, et al., Antigen-specific human antibodies from mice comprising four distinct genetic modifications. Nature. Apr. 28, 1994;368(6474):856-9.

Morrison, Immunology. Success in specification. Nature. Apr. 28, 1994;368(6474):812-3.

Fishwild, et al., High-avidity human IgG kappa monoclonal antibodies from a novel strain of minilocus transgenic mice. Nat Biotechnol. Jul. 1996;14(7):845-51.

Lonberg, et al., Human antibodies from transgenic mice. Int Rev Immunol. 1995;13(1):65-93.

Edgar, et al., Gene Expression Omnibus: NCBI gene expression and hybridization array data repository. Nucleic Acids Res. Jan. 1, 2002;30(1):207-10.

Pan, A comparative review of statistical methods for discovering differentially expressed genes in replicated microarray experiments. Bioinformatics. Apr. 2002;18(4):546-554.

Tamayo, et al., Interpreting patterns of gene expression with self-organizing maps: methods and application to hematopoietic differentiation. Proc Natl Acad Sci U S A. Mar. 16, 1999;96(6):2907-12.

Vitali, et al., Classification criteria for Sjögren's syndrome: a revised version of the European criteria proposed by the American European Consensus Group. Ann Rheum Dis. Jun. 2002;61(6):554-8.

Shiboski, et al., American College of Rheumatology classification criteria for Sjögren's syndrome: a data-driven, expert consensus approach in the Sjögren's International Collaborative Clinical Alliance cohort. Arthritis Care Res (Hoboken). Apr. 2012;64(4):475-87.

Bohan, et al., Polymyositis and dermatomyositis (first of two parts). N Engl J Med. Feb. 13, 1975;292(7):344-7.

Bohan, et al., Polymyositis and dermatomyositis (second of two parts). N Engl J Med. Feb. 20, 1975;292(8):403-7.

Casciola-Rosen, et al., Enhanced autoantigen expression in regenerating muscle cells in idiopathic inflammatory myopathy. J Exp Med. Feb. 21, 2005;201(4):591-601.

De Hoon, et al., Open source clustering software. Bioinformatics. Jun. 2004;20(9):1453-1454.

Eisen, et al., Cluster analysis and display of genome-wide expression patterns. PNAS. Dec. 1998;95(25):14863-14868.

Levine, et al., Novel conformation of histidyl-transfer RNA synthetase in the lung: the target tissue in Jo-1 autoantibody-associated myositis. Arthritis Rheum. Aug. 2007;56(8):2729-39.

Yao, et al., Type I interferon: potential therapeutic target for psoriasis? PLoS One. Jul. 16, 2008;3(7):e2737.

Druker, et al., Efficacy and safety of a specific inhibitor of the BCR-ABL tyrosine kinase in chronic myeloid leukemia. N Engl J Med. Apr. 5, 2001;344(14):1031-7.

Radich, et al., Gene expression changes associated with progression and response in chronic myeloid leukemia. Proc Natl Acad Sci U S A Feb. 21, 2006; 103(8): 2794-2799.

\* cited by examiner

METHODS FOR IDENTIFYING PATTERNS OF IFN INDUCED EXPRESSION AND USE IN DIAGNOSIS, MONITORING AND THERAPY

REFERENCE TO RELATED APPLICATIONS

This application is a Divisional application of U.S. patent application Ser. No. 14/401,655, filed Nov. 17, 2015, which is a 35 U.S.C. § 371 U.S. national entry of International Application PCT/US2013/040843, having an international filing date of May 14, 2013, and claims the benefit of U.S. Provisional Patent Application No. 61/648,251, filed on May 17, 2012, all of which are hereby incorporated by reference for all purposes as if fully set forth herein.

STATEMENT OF GOVERNMENTAL INTEREST

This invention was made with government support under grant nos. DE012354, AR044684, awarded by the National Institutes of Health. The government has certain rights in the invention.

BACKGROUND OF THE INVENTION

Defining molecular pathways with precision in pathological tissues has important implications in terms of diagnosis, disease subsetting, monitoring, and therapy. This concept is well illustrated in cancer, where recent studies have demonstrated that very similar clinical and pathological phenotypes encompass multiple molecular subtypes, contributing to different responses to therapy. It is widely acknowledged that significant heterogeneity exists among patients with autoimmune rheumatic diseases, in terms of phenotype, clinical course, and response to therapy. With the increasing availability of therapies that target specific immune pathways, it has become a priority to define whether the activation of distinct molecular pathways identifies specific subsets of patients within broader phenotypes. The IFN pathways, which have been implicated in the pathogenesis of autoimmune rheumatic diseases, are particularly relevant in this regard.

Sjögren syndrome (SS) is a chronic autoimmune inflammatory disease that targets exocrine glands, particularly salivary and lacrimal glands. Significant evidence implicates IFNs in the pathogenesis of SS including the following: (i) increased levels of circulating IFNs in the plasma of SS patients; (ii) expression of IFN-regulated genes in minor salivary gland biopsies from SS patients; (iii) the presence of a prominent IFN signature in circulating monocytes and peripheral blood mononuclear cells (PBMCs) from SS patients; and (iv) the enrichment of plasmacytoid dendritic cells in SS salivary glands. Similar IFN signatures have been observed in other rheumatic diseases, including dermatomyositis (DM), polymyositis, scleroderma, and systemic lupus erythematosus (SLE). Interestingly, although several recent papers have suggested that these inflammatory diseases might benefit from inhibition of the type I IFN pathway, studies have shown that inhibition of IFN-α signaling in psoriasis patients (whose skin expresses a prominent IFN signature) had no clinical effect. Such data suggest that interpretation of the IFN signature is likely more nuanced than initially conceived, and that additional understanding of the components and mechanisms of the IFN signature is essential. In particular, although the IFN signatures observed in blood and tissues of patients with immune-mediated rheumatic diseases have been attributed to the activity of type I IFNs (e.g. IFN-α, IFN-β), contributions of type II IFN (IFN-γ) have not been systematically pursued.

The failure of a recent trial of an anti-IFN-α monoclonal antibody in psoriasis (which expresses a strong IFN signature), coupled with the finding that expression of IFN signatures is prominent in many different inflammatory diseases, underscores the need to improve our understanding of the origins and meaning of the IFN signature in different inflammatory diseases in vivo.

Quantification of the specific markers of both type I and type II IFN activity is essential to define the origin of the IFN-induced protein expression pattern seen in cells and tissues, and there exists a need for improved methods for identifying specific markers of both type I and type II IFN activity which will lead to improved disease subsetting, monitoring, and identification of improved therapies.

SUMMARY OF THE INVENTION

In accordance with one or more embodiments of the present invention, the inventors initially defined the genes induced by type I and type II IFNs in a human submandibular gland (HSG) epithelial cell line. Unexpectedly, it was found that the majority of genes that are highly up-regulated by IFN-α are also highly induced by IFN-γ. In contrast, there was a substantial group of genes that are highly induced by IFN-γ only. To determine whether type I or type II IFN activity was present in minor salivary gland biopsies from patients with SS, precise probes were selected and validated that report on the distinct IFN pathways. Protein expression in minor salivary gland biopsies from SS patients and controls was evaluated by immunoblotting and immunohistochemistry. IFN-regulated proteins were expressed at high levels in SS patients in a pattern consistent with the activity of both type I and type II IFN. However, there was heterogeneity between patients, with evidence of type I IFN-preferential or IFN-γ-preferential patterns. The dominant pattern in SS was quite distinct from that seen in DM, where a more prominent type I IFN pattern was evident. In SS, the cellular distribution of probes of different IFN pathways was also noteworthy: IFN-γ-specific probes were localized to salivary epithelial cells and inflammatory cells in adjacent regions, whereas IFN-α-preferential markers were expressed mostly in salivary epithelial cells in regions that also demonstrate IFN-γ activity. Recent analysis of minor salivary gland biopsies from an additional 53 SS patients confirms the presence of IFN pathway activity in a subset of patients (47%). Furthermore, IFN activity was heterogeneous, with IFNα-predominance in 8 patients, IFNγ-predominance in 6 patients and evidence of both IFNα and IFNγ activity in 11 patients.

In accordance with an embodiment, the present invention provides a method for establishing the IFN expression profile of a tissue comprising: a) preparing a protein lysate from the tissue sample of the subject; and b) analyzing the tissue lysate of a) for the presence of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, and GBP5 proteins.

In accordance with another embodiment, the present invention provides a method for establishing the IFN expression profile of a tissue from a subject suspected of having a rheumatic disease comprising: a) preparing a protein lysate from the tissue sample of interest from the subject; b) analyzing the tissue lysate of a) for the presence of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5, plus a loading control protein (e.g. β-actin or vinculin proteins); c) normalizing the expression levels of MDA5, IFIT3, GBP1, GBP2, INDO, UBD, IRF1, RARRES3, WARS, CXCL10, IL18BP, SERPING1, or GBP5 proteins in the subject sample to the expression levels of β-actin or vinculin in the same sample; d) comparing the normalized expression levels of MDA5, IFIT3, GBP1, GBP2, INDO, UBD, IRF1, RARRES3, WARS, CXCL10, IL18BP, SERPING1, or GBP5 in a patient sample against the same proteins in a control sample; and e) determining that the subject has evidence of type I IFN or type II IFN activity when the expression levels of one or more of the proteins are increased at least 3 standard deviations over the levels in the control sample.

In accordance with a further embodiment, the present invention provides a method for establishing the IFN expression profile of a tissue comprising: a) obtaining mRNA from the tissue sample of interest from the subject; and b) analyzing the mRNA of a) for the presence of mRNA encoding at least one of marker of type I IFN activity (e.g. MDA5 or IFIT3), plus at least one marker of type II IFN activity: GBP1, GBP2, INDO, UBD, IRF1, RARRES3, WARS, CXCL10, IL18BP, SERPING1, GBP5.

In accordance with yet another embodiment, the present invention provides a method for establishing the IFN expression profile of a tissue from a subject suspected of having a rheumatic disease comprising: a) obtaining mRNA from the tissue sample of interest from the subject; b) analyzing the mRNA of a) for the presence of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5; c) comparing the levels of MDA5, IFIT3, GBP1, GBP2, INDO, UBD, IRF1, RARRES3, WARS, CXCL10, IL18BP, SERPING1, and GBP5 mRNA in the subject sample to the levels of the same mRNA in a control sample; and d) determining that the subject has evidence of type I IFN or type II IFN activity when the expression levels of one or more of the mRNAs of interest are increased when compared to the levels in the control sample.

In accordance with an embodiment, the present invention provides a kit for establishing the IFN expression profile of a tissue from a subject, comprising: one or more ligand(s) for determining the levels or concentration of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 in a tissue sample from a subject.

In accordance with another embodiment, the present invention provides in vitro use of an antibody binding at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 for establishing the IFN expression profile of a tissue from a subject suspected of having evidence of IFN-α or IFN-γ activity comprising: a) preparing a protein lysate from the tissue sample of the subject; b) analyzing the tissue lysate of a) for the presence of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 proteins, and a loading control protein (e.g. β-actin and vinculin); c) normalizing the expression levels of MDA5, IFIT3, GBP1, GBP2, INDO, UBD, IRF1, RARRES3, WARS, CXCL10, IL18BP, SERPING1, GBP5 proteins in the subject sample to the expression levels of β-actin or vinculin in the same sample; d) comparing the normalized expression levels of MDA5, IFIT3, GBP1, GBP2, INDO, UBD, IRF1, RARRES3, WARS, CXCL10, IL18BP, SERPING1, GBP5 protein in a patient sample against the same proteins in a control sample; and e) determining that the subject has evidence of type I IFN or type II IFN activity when the expression levels of one or more of the proteins are increased at least 3 standard deviations over the levels in the control sample.

In accordance with a further embodiment, the present invention provides a device adapted for carrying out any of the methods described herein, comprising: a) an analyzing unit comprising one or more antibodies binding at least one of MDA5 or IFIT3, and at least one of GBP1, GBP2, INDO, UBD, IRF1, RARRES3, WARS, CXCL10, IL18BP, SERPING1, and GBP5 proteins, the unit being adapted for determining the level of at least one of MDA5, IFIT3, GBP1, GBP2, INDO, UBD, IRF1, RARRES3, WARS, CXCL10, IL18BP, SERPING1, and GBP5 proteins in a first and second sample from an individual; and b) an evaluation unit for comparing the determined level in the first sample with the level in the second sample whereby a rheumatic disease can be diagnosed, the unit comprising a database with the levels of at least one of MDA5, IFIT3, GBP1, GBP2, INDO, UBD, IRF1, RARRES3, WARS, CXCL10, IL18BP, SERPING1, and GBP5 proteins in the first sample to the second sample, and a computer-implemented algorithm for carrying out a comparison step.

DETAILED DESCRIPTION OF THE INVENTION

Figure 1:
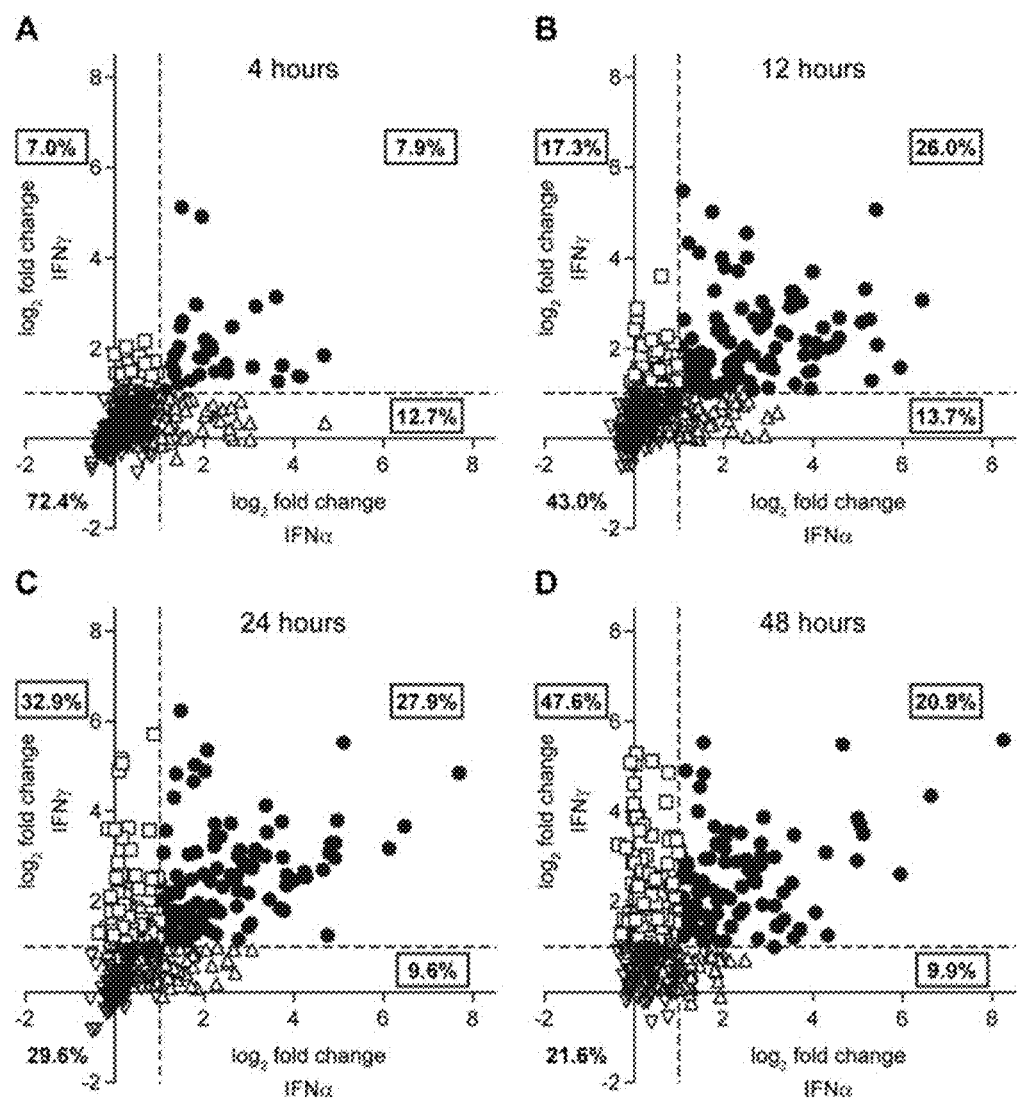
FIG. 1 depicts temporal analysis of IFN-α and IFN-γ responses in HSGs. Expression of the 416 IFN-inducible transcripts at (A) 4, (B) 12, (C) 24, and (D) 48 hours. Data are presented as $\log_2$ fold change in expression relative to untreated cells. The transcripts in each group are represented as follows: IFN-γ specific (open squares), IFN-α/γ responsive (circles), IFN-α specific (open triangles), and uninduced (inverted open triangles). The percentage of transcripts in each group is listed. The dashed lines indicate a twofold increase in expression.

The autoimmune rheumatic diseases are a complex group of disorders that display considerable heterogeneity in phenotype, immune response, disease course, and response to therapy. Defining whether distinct molecular subgroups exist may facilitate novel disease classification and allow more precise selection of therapy. The IFN pathways are particularly relevant in this regard.

The finding of an IFN signature in the blood and tissue of many autoimmune inflammatory diseases has important potential for disease monitoring and therapy. Although there is significant evidence implicating type I IFNs in the generation of the IFN signature in SLE, it remains unclear whether type I IFNs are the primary driver of the IFN signature in other rheumatic processes. Indeed, previous microarray studies have shown that, although IFN-induced proteins are differentially expressed in SS salivary glands relative to controls, the activities of IFN-α and IFN-γ could not be distinguished. The enrichment of activated lymphocytes (robust sources of IFN-γ secretion) in inflamed tissues in the rheumatic diseases reinforces the possible contributions of IFN-γ to the IFN signature observed in tissues.

Previous studies analyzing IFN-induced gene expression in various cell types in vitro have been limited in their ability to interpret signatures observed in tissues, because they frequently only address a single time point and use arbitrary doses of IFN. Diseased tissues encompass events that have occurred asynchronously before tissue sampling. Extensive gene expression analysis was herein performed to determine the kinetics of the responses and identify probes that differentiate between type I and type II IFN effects at multiple time points. Because autoantigen expression in target tissues is likely a critical partner in driving the autoimmune response, in accordance with the inventive methods, doses of IFN-α and IFN-γ were selected that induced equivalent amounts of Ro52, an IFN-induced autoantigen frequently targeted in SS. The extensive similarity of the patterns of gene expression in response to type I and type II IFNs was quite remarkable. Of the gene products induced twofold or more by IFN-α, 38% (at 4 hours) to 74% (at 24 hours) were also induced twofold or more by IFN-γ. Interestingly, the IFN signatures defined to date in rheumatic disease samples largely include these IFN-α/γ-induced genes. These signatures cannot discriminate between the effects of type I and type II IFNs.

In accordance with one or more embodiments of the present invention, a cassette of molecules whose expression is strongly induced by, and highly specific for, type II IFN activity (e.g., CXCL10, GBP1, GBP2, GBP5, IRF1, IL18BP, INDO, RARRES3, SERPING1, UBD and WARS) across all time points after IFN exposure is provided. Given the high degree of specificity of the defined probes for IFN-γ effects, these markers should be included in analyses of IFN responses in tissues, to either confirm, or rule out, IFN-γ activity. The present inventive methods also highlight the importance of recognizing the cellular and kinetic heterogeneity of tissues when interpreting gene expression patterns in health and disease. Definition of specific markers of pathways, which maintain their specificity across a range of times, is both feasible and useful.

The present inventive methods use these tools to quantify the origins of IFN signatures in normal and diseased human tissues. Because multiple pathways may be activated simultaneously in diseased tissue, the inventive methods utilize a combination of IFN-α-preferential probes with IFN-γ-specific probes was used to quantify the activity of the different IFN pathways. Heterogeneity in IFN pathway activation was observed in different SS salivary glands. In most patients, evidence of both type I and II IFN activity was present. In some patients, there was evidence of either predominant type I (patient SS6) or type II IFN activity (patient SS7). Further analysis has demonstrated considerable heterogeneity of IFN activity in SS minor salivary gland biopsies. In a separate study, 25 of 53 patients (47%) have measurable IFN activity. Of these 25 patients, 6 demonstrate predominantly IFN-γ activity, 8 exhibit predominantly IFN-α activity and 11 have evidence of both IFNα and IFNγ activity. This was in contrast to a small cohort of DM patients who exhibited predominantly IFN-α activity. The at least four probes chosen in the initial analysis could identify relevant subgroups when protein expression in biopsies was quantified by densitometry, normalized against a loading control, and subjected to unsupervised hierarchical clustering. Diseased tissues were clearly separated from control tissues. Quite strikingly, SS tissues were separated from DM tissues, except for the single SS outlier that exhibited a predominantly type I IFN pattern, which clustered with DM patients.

It is has been found that just two or more IFN-induced proteins were sufficient to distinguish these groups.

The methods of the present invention are simple and quantitative, require very small amounts of tissue, provide an integrated readout of pathways active in the target tissues, and have the potential for automation. These inventive methods facilitate a more precise classification of patients based on activity of specific pathways in the target tissue. The inventive methods can be used as a molecular diagnostic to more precisely delineate disease subsets, and assist in selecting patients for therapy or for monitoring effectiveness.

The terms "sample," "patient sample," "biological sample," and the like, encompass a variety of sample types obtained from a patient, individual, or subject and can be used in a diagnostic, prognostic or monitoring assay. The patient sample may be obtained from a healthy subject, a diseased patient including, for example, a patient having associated symptoms of a rheumatic disease. Moreover, a sample obtained from a patient can be divided and only a portion may be used for diagnosis, prognosis or monitoring. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a salivary gland sample. In another embodiment, a sample of muscle tissue is used. In other embodiments, a sample comprises a blood or serum sample. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The terms "providing a sample" and "providing a biological (or patient) sample" are used interchangeably and mean to provide or obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, can also be used.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. The term, "amino acid analogs" refers to compounds that have the same basic chemical structure as a naturally occurring amino acid, e.g., an .alpha. carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of ordinary skill in the art recognizes that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typical conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the KIT nucleic acids, proteins and antibodies at any position. Any method known in the art for conjugating the antibody to the label may be employed, e.g., using methods described in Hermanson, Bioconjugate Techniques 1996, Academic Press, Inc., San Diego.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab').sub.2, Fab, Fv and rIgG. See also, Pierce Catalog and Handbook, 1994-1995 (Pierce Chemical Co., Rockford, Ill.). See also, e.g., Kuby, J., Immunology, 3.sup.rd Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., Nature Biotech. 14:309-314 (1996), or by immunizing an animal with the antigen or with DNA encoding the antigen.

Typically, an immunoglobulin has a heavy and light chain Each heavy and light chain contains a constant region and a variable region, (the regions are also known as "domains"). Light and heavy chain variable regions contain four framework" regions interrupted by three hypervariable regions, also called complementarity-determining regions (CDRs).

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332:323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The term "fully human antibody" refers to an immunoglobulin comprising human hypervariable regions in addition to human framework and constant regions. Such antibodies can be produced using various techniques known in the art. For example in vitro methods involve use of recombinant libraries of human antibody fragments displayed on bacteriophage (e.g., McCafferty et al., 1990, Nature 348: 552-554; Hoogenboom & Winter, J. Mol. Biol. 227:381 (1991); and Marks et al., J. Mol. Biol. 222:581 (1991)), yeast cells (Boder and Wittrup, 1997, Nat Biotechnol 15:553-557), or ribosomes (Hanes and Pluckthun, 1997, Proc Natl Acad Sci USA 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584, 5,545,807; 5,545,806; 5,569,825; 5,625, 126; 5,633,425; 5,661,016, and in the following scientific publications: (e.g., Jakobavits, Adv Drug Dehv Rev. 31:33-42 (1998), Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance See, e.g., Epitope Mapping Protocols in Methods in Molecular Biology, Vol. 66, Glenn E. Morris, Ed (1996).

Antibodies can be used to detect proteins stimulated by type I and/or type II IFN in the methods of the invention. The detection and/or quantification of proteins stimulated by type I and/or type II IFN can be accomplished using any of a number of well recognized immunological binding assays. A general overview of the applicable technology can be found in Harlow & Lane, Antibodies: A Laboratory Manual (1988) and Harlow & Lane, Using Antibodies (1999). Other resources include see also Methods in Cell Biology: Antibodies in Cell Biology, volume 37 (Asai, ed. 1993); Basic and Clinical Immunology (Stites & Ten, eds., 7th ed. 1991, and Current Protocols in Immunology (Coligan, et al. Eds, John C. Wiley, 1999-present). Immunological binding assays can use either polyclonal or monoclonal antibodies.

Commonly used assays include noncompetitive assays (e.g., sandwich assays) and competitive assays. In competitive assays, the amount of genes expression products stimulated by type I and/or type II IFN present in the sample is measured indirectly by measuring the amount of a known, added (exogenous) expression product displaced (competed away) from an anti-expression product antibody by the unknown present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers, which are then detected according to standard techniques (see Monroe et al., Amer. Clin. Prod. Rev. 5:34-41 (1986)).

Immunoassays also often use a labeling agent to specifically bind to and label the complex formed by the antibody and antigen. The labeling agent may itself be one of the moieties comprising the antibody/antigen complex. Thus, the labeling agent may be a labeled for gene products stimulated by type I and/or type II IFN or a labeled anti-type I or type II IFN antibody. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. The labeling agent can be modified with a detectable moiety, such as biotin, to which another molecule can specifically bind, such as streptavidin. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent compounds (e.g., fluorescein isothiocyanate, Texas red, rhodamine, fluorescein, and the like), radiolabels, enzymes (e.g., horse radish peroxidase, alkaline phosphatase and others commonly used in an ELISA), streptavidin/biotin, and colorimetric labels such as colloidal gold or colored glass or plastic beads (e.g., polystyrene, polypropylene, latex, etc.). Chemiluminescent compounds may also be used. For a review of various labeling or signal producing systems that may be used, see U.S. Pat. No. 4,391,904.

In accordance with another embodiment, the present invention provides in vitro use of an antibody binding one at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 for establishing the IFN expression profile of a tissue from a subject suspected of having a rheumatic disease comprising: a) preparing a protein lysate from the tissue sample of the subject; b) analyzing the tissue lysate of a) for the presence of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5; c) comparing the expression levels of MDA5, IFIT3, GBP1, GBP2, INDO, UBD, IRF1, RARRES3, WARS, CXCL10, IL18BP, SERPING1, and GBP5 proteins in the subject sample to the expression levels of the same proteins in a control sample; and d) determining that the subject has evidence of IFN-$\alpha$ or IFN-$\gamma$ activity when the expression levels of one or more of the proteins are increased at least 3 S.D. over the levels in the control sample As used herein, the term "control sample" or "reference sample" means a sample from a subject known not to have a rheumatic disease or immune disorder.

The term "comparing" as used herein encompasses comparing the level of the peptide or polypeptide comprised by the sample to be analyzed with a level of a suitable reference level specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample or a ratio of amounts is compared to a reference ratio of amounts. The comparison referred to in the methods of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format.

Moreover, the present invention relates to a device adapted for carrying out the method of the present invention for diagnosing or predicting an outcome for a rheumatic disease comprising, in an embodiment, a. an analyzing unit comprising one or more binding ligand which specifically binds to at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 proteins, the unit being adapted for determining the level of MDA5, IFIT3, GBP1, GBP2, INDO, UBD, IRF1, RARRES3, WARS, CXCL10, IL18BP, SERPING1, and GBP5 proteins in a first and a second sample from an individual; and, b. an evaluation unit for comparing the determined level in the first sample with the level in the second sample whereby a rheumatic disease progression or outcome can be diagnosed, the unit comprising a database with the level of MDA5, IFIT3, GBP1, GBP2, INDO, UBD, IRF1, RARRES3, WARS, CXCL10, IL18BP, SERPING1, and GBP5 proteins in the first sample as compared to the second sample, the levels being, preferably, derived from an individual or a group of individuals known to have developed rheumatic diseases or more preferably derived from an individual or a group of individuals known not to have developed rheumatic diseases and a computer-implemented algorithm for carrying out a comparison step. It is to be understood that the definitions and explanations of the terms made above and below apply for all embodiments described in this specification and the accompanying claims (except stated otherwise). In the context of the aforementioned device, the reference levels are preferably derived from a sample of (reference) individuals as defined above. It will be understood by those of skill in the art that other proteins which are specifically induced by type I or type II IFNs can be used with the inventive methods.

The term "device" as used herein relates to a system comprising the aforementioned units operatively linked to each other as to allow the diagnosis or monitoring according to the methods of the invention. Preferred detection agents which can be used for the analyzing unit are disclosed elsewhere herein. The analyzing unit, preferably, comprises the detection agents in immobilized form on a solid support which is to be contacted to the sample comprising the biomarkers the level of which is to be determined. Moreover, the analyzing unit can also comprise a detector which determines the level of binding ligand which is specifically bound to the biomarker(s). The determined level can be transmitted to the evaluation unit. The evaluation unit comprises a data processing element, such as a computer, with an implemented algorithm for carrying out a comparison between the determined level and a suitable reference (e.g. a reference level, or the level of the marker in a first or second sample from the individual). Suitable references can be derived from samples of individuals to be used for the generation of reference levels as described elsewhere herein above. The results may be given as output of parametric diagnostic raw data, preferably, as absolute or relative levels. It is to be understood that these data will need interpretation by the clinician. However, also envisaged are expert system devices wherein the output comprises processed diagnostic raw data the interpretation of which does not require a specialized clinician.

In accordance with a further embodiment, the present invention provides device adapted for carrying out any of the methods described herein, comprising: a) an analyzing unit comprising one or more antibodies binding at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5, the unit being adapted for determining the level of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 proteins in a first and second sample from an individual; and b) an evaluation unit for comparing the determined level in the first sample with the level in the second sample whereby an increase in IFN-α and/or IFN-γ levels can be diagnosed, the unit comprising a database with the levels of at least one marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 proteins in the first sample to the second sample, and a computer-implemented algorithm for carrying out a comparison step.

The methods of the present invention can be used for diagnosis, prognosis and/or treatment monitoring of rheumatic diseases in a subject. For example, as described herein, the amount of expression of genes induced by type I and/or type II IFNs expressed in a specific tissue of a subject can be used to determine the severity and type of immunological condition of the subject as well as determine whether an ongoing treatment is having an effect by comparing expression levels of genes induced by type I and/or type II IFNs before, during, and after treatment.

It will be understood by those of ordinary skill in the art, that in some embodiments, the determination of an increase in IFN-α and/or IFN-γ levels can be diagnosed using the expression levels of at least marker of type I IFN activity (e.g. MDA5 or IFIT3), and at least one marker of type II IFN activity: GBP1, GBP2, INDO, UBD, IRF1, RARRES3, WARS, CXCL10, IL18BP, SERPING1, GBP5 proteins. In other embodiments, the determination of an increase in IFN-α and/or IFN-γ levels can be diagnosed using the expression levels of at least three, four, or 5 or more of MDA5, IFIT3, GBP1, GBP2, INDO, UBD, IRF1, RARRES3, WARS, CXCL10, IL18BP, SERPING1, and GBP5 proteins.

The invention also provides kits for diagnostic, prognostic or therapeutic applications. For diagnostic/prognostic applications, such kits may include any or all of the following: assay reagents, buffers, mRNA, PCR, qPCR probes, primers, antibodies, or the like. Moreover, the kit may, preferably, comprise standards, reference samples and control samples. In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

It will be understood by those of skill in the art that the inventive methods can be used to aid in the treatment of rheumatic diseases by identifying a particular expression profile of type I or type II IFN induced genes and then administering to the subject suitable medicaments for treatment including for example, recombinant antibodies which bind and neutralize IFNs in circulation, recombinant type I or type II IFN receptors which bind and neutralize circulating type I or type II IFN, other compounds which bind and inhibit the function of IFNs.

EXAMPLES

Cell Culture and IFN Treatment. Cells from an HSG epithelial cell line, a gift from Bruce Baum (National Institutes of Health/National Institute of Dental and Craniofacial Research, Bethesda, Md.), were maintained in MEM supplemented with 10% (vol/vol) FBS and 2 mM 1-glutamine. Cells were cultured as noted in the presence of purified leukocyte IFN-α (Sigma) or IFN-γ (R&D Systems).

Microarray Analysis. HSGs were cultured for 4, 12, 24, or 48 hours either with IFN-α (1,000 U/mL) or IFN-γ (50 ng/mL), or without IFN added, and samples were collected in triplicate at each time point; 36 total samples were assayed. Total RNA was extracted using TRIzol (Invitrogen). Additional purification was performed on RNeasy columns (Qiagen), and total RNA quality was assessed using an Agilent 2100 Bioanalyzer (Agilent Technologies). Biotin-labeled cRNA was prepared from total RNA according to the chip manufacturer's protocol (Illumina). cRNA was hybridized to Illumina Human HT12 v3 Expression BeadChips, and signal was detected with streptavidin-Cy3. Signal intensity quantification was performed using an Illumina BeadStation 500GX Genetic Analysis Systems scanner. The microarray data discussed in this publication have been deposited in the National Center for Biotechnology Information's Gene Expression Omnibus (Nucleic Acids Res 30(1):207-210 (2002)).

Analytical Methods and Statistical Analysis for Microarray Data. A single intensity (expression) value for each Illumina probe was obtained using Illumina BeadStudio software with standard settings and no background correction. The expression values for all of the probes for each sample were scaled to have median of 256 ($2^8$) and then $\log_2$ transformed. Gene expression in IFN-α- and IFN-γ-treated cells was compared against untreated cells at each time point. Transcripts (i.e., Illumina probes) considered to be differentially expressed between two groups of samples were those satisfying the following criteria: (i) Welch t test values of $P \leq 0.01$ (Bioinformatics 18(4):546-554 (2002)); (ii) Benjamini-Hochberg FDR of $\leq 0.25$ (35); (iii) a fold change of >2.0 (calculated using geometric means); and (iv) the expression value of the transcript is above the Illumina BeadStudio calculated background (detection P value of <0.01) in all three samples in the group with the higher average expression level for that probe, thus avoiding false positives based on background noise and also reducing the number of statistical tests for the subsequent FDR calculation. For a given probe, if the average of the expression levels in the control samples is greater than that for the IFN-treated samples, then the ratio of the control average to the IFN average is given, with a minus sign in front, so the fold change magnitude is always at least 1. SOM analysis was performed in GenePattern 2.0 using the SOM clustering algorithm with final a and 6 values of 0.005 and 0.5, respectively (Proc Natl Acad Sci USA 96(6):2907-2912 (1999)).

Patients and Tissues. One set of minor salivary gland (MSG) biopsies was obtained with informed consent from individuals undergoing diagnostic evaluation for sicca symptoms indicative of SS, under the approval of the Ethical Committee of School of Medicine of the National University of Athens (Athens, Greece; Protocol 5107). SS patients were diagnosed on the basis of the revised American-European classification criteria (Group. Ann Rheum Dis 61(6):554-558 (2002)). The control group included individuals complaining of sicca symptoms, who did not fulfill the aforementioned SS criteria and had negative biopsy focus scores (<1 foci/4 mm2). None of the individuals studied had evidence of lymphoma, sarcoidosis, or infection by hepatitis B, hepatitis C, or HIV. Frozen minor salivary gland biopsies (for lysate generation) were obtained from eight SS patients and six controls. Salivary gland paraffin sections were obtained from four SS patients and three controls. A second set of minor salivary gland biopsies was obtained with informed consent from individuals enrolled in the Sjögren's International Collaborative Clinical Alliance [SICCA], funded under contract N01 DE-32636 by the National Institute of Dental and Craniofacial Research, with funding support from the National Eye Institute and Office for Research in Women's Health. All studies were performed under the approval of the JHU IRB protocol NA 00079238. All patients satisfied the American College of Rheumatology Classification Criteria for Sjögren's syndrome Shiboski S C et al. Arthritis Care Res 2012; 64:475-487. None of the individuals studied had evidence of lymphoma, sarcoidosis, or infection by hepatitis B, hepatitis C, or HIV. The control group included individuals complaining of sicca symptoms, who did not fulfill the aforementioned SS criteria and had negative biopsy focus scores (<1 foci/4 mm2).

Muscle biopsies were obtained from patients seen at the Neuromuscular Clinic at Johns Hopkins Hospital. Informed consent was obtained from every study subject, and all samples were collected under the auspices of Johns Hopkins Medicine Institutional Review Board-approved protocols. All patient samples were deidentified, with clinical and laboratory features linked only to the patient code. Surgical procedures were performed for patient management, and the research tissue samples were excess tissue obtained for routine diagnostic purposes. Frozen muscle biopsies were obtained from four patients with DM and three individuals whose biopsies were histologically normal. Histologic criteria for biopsies identified as DM were consistent with Bohan and Peter criteria (N Engl J Med 292(7):344-347; N Engl J Med 292(8):403-407 (1975)).

Determination of Antigen Expression in Cultured Cells and Human Tissues. Lysates were prepared on ice as described previously (J Exp Med 201(4):591-601 (2005)). Protein equivalents were electrophoresed on SDS-polyacrylamide gels, transferred onto nitrocellulose membranes, and probed with antibodies recognizing GBP1, Ro52 (Santa Cruz Biotechnology), IFIT3, vinculin (Sigma-Aldrich), GBP2 (Novus Biologicals), or MDA5 (American Research Products). Visualization was performed using horseradish peroxidase-conjugated secondary antibodies (Jackson Immunoresearch) and developed using an enhanced chemiluminescence detection system (Pierce). For densitometry, X-ray films were scanned using an AGFA Arcus II scanner, and densities were quantified using Bio-Rad Quantity One software. Hierarchical clustering of protein expression was performed in GenePattern 2.0 using the Hierarchical Clustering algorithm (Bioinformatics 20(9):1453-1454 (2004)) and was visualized using Java TreeView (Proc Natl Acad Sci USA 95(25):14863-14868 (1998)).

Immunohistochemistry. Salivary gland paraffin sections were processed as described previously (Arthritis Rheum 56(8):2729-2739 (2007)). Briefly, after rehydration, antigen retrieval, and blocking, sections were incubated overnight at 4° C. with either anti-IFIT3 (10 µg/mL; Novus) or GBP2 antibodies (30 µg/mL; Novus Biologicals). HRP-conjugated secondary antibody incubations were performed for 1 hour at room temperature, and staining was visualized with diaminobenzidine (Dako) per the manufacturer's directions. Nuclei were counterstained with Mayer's hematoxylin. Negative controls were performed using isotype control antibodies, and in all cases no staining was detected. All images were captured using a Zeiss Axioskop 50 with a Zeiss AxioCam HRc camera and AxioVision 4 software.

Example 1

Genes Most Strongly Induced by IFN-α are also Induced by IFN-γ. To define the origin of the IFN signature in minor salivary gland biopsies from patients with SS, microarray studies were initially performed in an HSG cell line to define IFN-α and IFN-γ responses in a disease-relevant cell type. Concentrations of IFN-α and IFN-γ were selected that induced equivalent levels of Ro52 expression (IFN-α, 1,000

U/mL; IFN-γ, 50 ng/mL) (data not shown). Ro52 was set as our reference molecule, because it is a frequent autoantigen in SS and is known to be induced by both IFN-α and IFN-γ. Because protein expression in target tissues provides an integrated view of events that have occurred over time before biopsy, IFN-induced gene expression was analyzed at 4, 12, 24, and 48 hours. 416 mRNA transcripts were identified that were significantly induced [fold change, ≥2.0; value of P≤0.01; false discovery rate (FDR), ≤0.25] by IFN-α or IFN-γ at one or more time points.

The induction of all 416 transcripts by IFN-α and IFN-γ was first compared at each time point and made several important observations (FIG. 1 A-D): (i) The largest number of IFN-α-induced transcripts (n=165) was seen at 12 hours (FIG. 1B). In contrast, the IFN-γ response lagged significantly, with the maximal number of IFN-γ-induced transcripts (n=285) detected at 48 hours (FIG. 1D); (ii) There were few transcripts exclusively induced by IFN-α at any time point (FIG. 1 A-D, triangles); except for a single transcript at 4 hours (FIG. 1A), all IFN-α-specific transcripts were induced eightfold (i.e., a log 2 fold change of 3) or less. Notably, however, >50% of IFN-γ-responsive transcripts were induced exclusively by IFN-γ (FIGS. 1 C and D, squares). Of these, 10 were induced eightfold or greater at 24 hours and 23 were induced eightfold or greater at 48 hours; (iii) The majority of transcripts induced highly by IFN-α were also induced by IFN-γ (FIG. 1 A-D, circles). Additionally, the levels of induction by IFN-α were significantly higher in the IFN-α/γ-responsive group than the IFN-α-specific group (at 24 hours, P=0.01; Wilcoxon rank sum test) (FIG. 1C). Similarly, the levels of induction by IFN-γ were higher in the IFN-α/γ-responsive group than the IFN-γ-specific group (at 24 hours, P=5.4×10-12; Wilcoxon rank sum test).

Example 2

To identify groups of probes that distinguish between the activity of IFN-α and IFN-γ across all time points, gene expression data were subjected to unsupervised clustering using self-organizing maps (SOMs). The 416 IFN-induced transcripts were clustered into 16 groups, and the mean level of induction in response to IFN-α and IFN-γ at each time point was calculated for each group. Mean induction was compared across all groups, and several major findings were evident. First, there are few transcripts that are specific reporters of an IFN-α response. Of the four groups of transcripts (n=65) (FIG. 2 A-D) that exhibited the highest mean induction in response to IFN-α, three groups (n=45) (FIG. 2 A-C) were induced on average fourfold or greater by IFN-γ at two or more time points. Interestingly, many of the genes associated with the IFN signature defined in DM and SLE were among these transcripts (Table 1), highlighting that these signatures are not necessarily IFN-α specific. In contrast, two of the three groups of transcripts (n=34) with the highest mean induction by IFN-γ (FIGS. 2 A, E, and F) were either exquisitely specific (FIG. 2E; n=12) or highly preferential (FIG. 2F; n=11) for IFN-γ activity. An additional four groups (n=87) of transcripts exhibited either low differential expression, which occurred at only one time point, or were IFN-γ specific only at 48 hours (data not shown). The remaining six groups, which included the majority of IFN-responsive transcripts (n=241; 57.9%), were induced, on average, less than fourfold by IFN-α and IFN-γ across all time points (data not shown). Thus, these probes have limited utility as markers of an IFN response. These data demonstrate that detecting genes highly induced by IFN-α cannot distinguish clearly between the activity of IFN-α and IFN-γ, particularly if the timing of the stimulus is unknown. In contrast, quantifying markers uniquely and highly induced by IFN-γ provides a useful set of probes to distinguish the origin of an IFN signature observed in vivo.

TABLE 1

Figure 2:
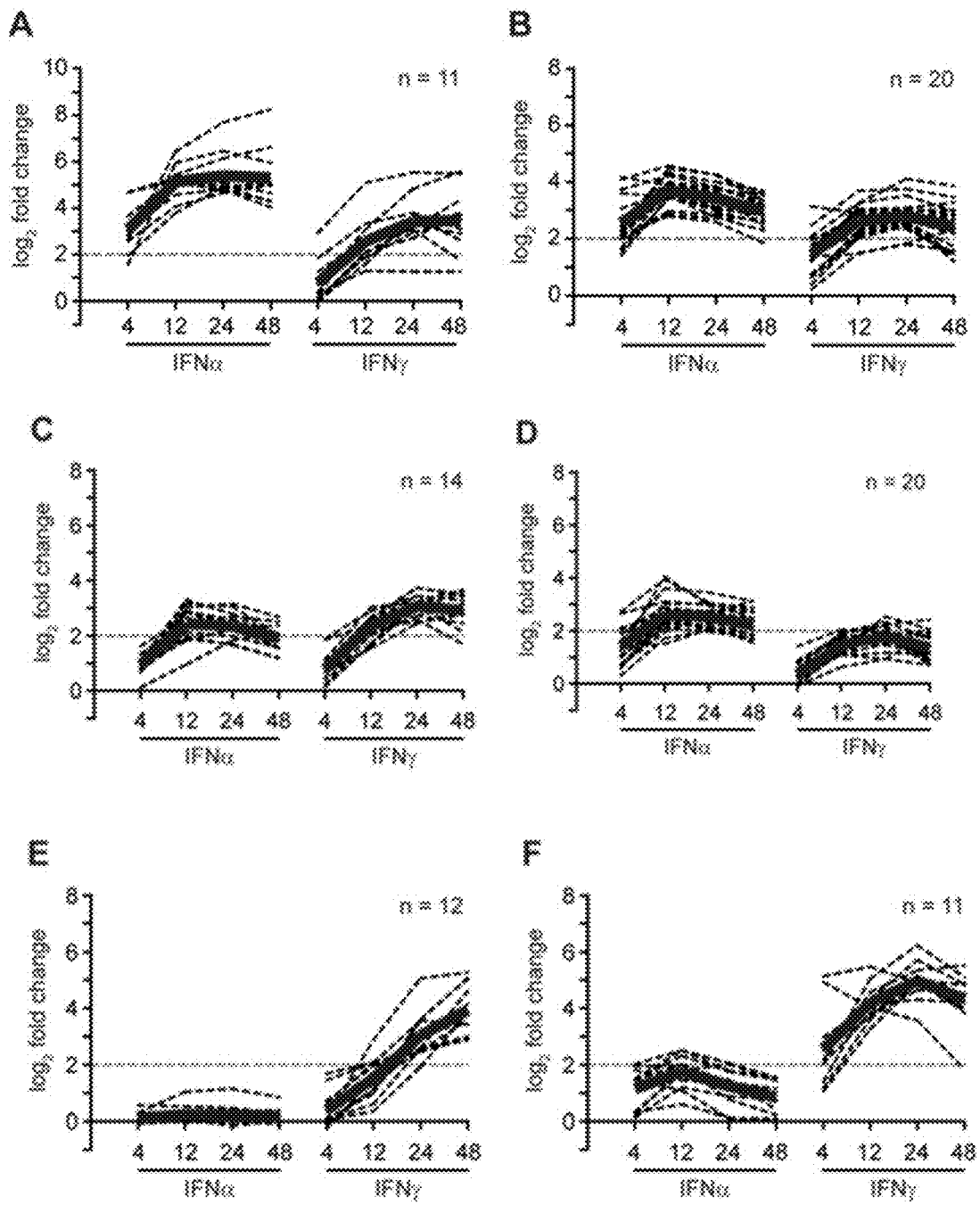
FIG. 2 depicts the analysis of IFN-inducible gene expression using self-organizing maps (SOMs). The 416 IFN-inducible transcripts were clustered into 16 groups. The mean induction values were calculated for each group of transcripts at each time point (4, 12, 24, or 48 hours) and the groups with the highest mean expression in response to IFN-α (A-D) and IFN-γ (A, E, and F) are shown. Individual transcripts are shown in dotted black (thin lines). Mean values for the group at each time point are shown with a thick black line. The y-axis represents $\log_2$ fold change in expression relative to untreated cells. The grey dashed lines indicate a fourfold increase in expression.

Lists of IFNα and IFNγ-responsive transcripts presented in FIG. 2

| Group | probe ID | Gene Symbol | Description |
|---|---|---|---|
| A | ILMN_1674063 | OAS2 | 2'-5'-oligoadenylate synthetase 2, 69/71 kDa, transcript variant 1 |
| A | ILMN_1687384 | IFI6 | Interferon, alpha-inducible protein 6, transcript variant 3 |
| A | ILMN_1701789 | IFIT3 | Interferon-induced protein with tetratricopeptide repeats 3 |
| A | ILMN_1707695 | IFIT1 | Interferon-induced protein with tetratricopeptide repeats 1, transcript variant 2 |
| A | ILMN_1723912 | IFI44L | Interferon-induced protein 44-like |
| A | ILMN_1760062 | IFI44 | Interferon-induced protein 44 |
| A | ILMN_1769520 | UBE2L6 | Ubiquitin-conjugating enzyme E2L 6, transcript variant 1 |
| A | ILMN_2054019 | ISG15 | ISG15 Ubiquitin-like modifier |
| A | ILMN_2058782 | IFI27 | Interferon, alpha-inducible protein 27, transcript variant 2 |
| A | ILMN_2347798 | IFI6 | Interferon, alpha-inducible protein 6, transcript variant 2 |
| A | ILMN_2410826 | OAS1 | 2',5'-oligoadenylate synthetase 1, 40/46 kDa, transcript variant 3 |
| B | ILMN_1658247 | OAS1 | 2',5'-oligoadenylate synthetase 1, 40/46 kDa, transcript variant 2 |
| B | ILMN_1675640 | OAS1 | 2',5'-oligoadenylate synthetase 1, 40/46 kDa, transcript variant 3 |
| B | ILMN_1678054 | TRIM21 | Tripartite motif-containing 21 |
| B | ILMN_1690105 | STAT1 | Signal transducer and activator of transcription 1, 91 kDa, transcript variant alpha |
| B | ILMN_1690921 | STAT2 | Signal transducer and activator of transcription 2, 113 kDa |

TABLE 1-continued

Lists of IFNα and IFNγ-responsive transcripts presented in FIG. 2

| Group | probe ID | Gene Symbol | Description |
|---|---|---|---|
| B | ILMN_1691364 | STAT1 | Signal transducer and activator of transcription 1, 91 kDa, transcript variant beta |
| B | ILMN_1703108 | UBE2L6 | Ubiquitin-conjugating enzyme E2L 6, transcript variant 1 |
| B | ILMN_1710937 | IFI16 | Interferon, gamma-inducible protein 16 |
| B | ILMN_1731224 | PARP9 | Poly (ADP-ribose) polymerase family, member 9 |
| B | ILMN_1731418 | SP110 | SP110 nuclear body protein, transcript variant b |
| B | ILMN_1739428 | IFI12 | Interferon-induced protein with tetratricopeptide repeats 2 |
| B | ILMN_1745374 | IFI35 | Interferon-induced protein 35 |
| B | ILMN_1745397 | OAS3 | 2'-5'-oligoadenylate synthetase 3, 100 kDa |
| B | ILMN_1745471 | IRF9 | Interferon regulatory factor 9 |
| B | ILMN_1777325 | STAT1 | Signal transducer and activator of transcription 1, 91 kDa, transcript variant alpha |
| B | ILMN_1787509 | PRIC285 | Peroxisomal proliferator-activated receptor A Interacting complex 285, transcript variant 2 |
| B | ILMN_1798181 | IRF7 | Interferon regulatory factor 7, transcript variant b |
| B | ILMN_1801246 | IFITM1 | Interferon induced transmembrane protein 1 (9-27) |
| B | ILMN_2239754 | IFI13 | Interferon-induced protein with tetratricopeptide repeats 3 |
| B | ILMN_2415144 | SP110 | SP110 nuclear body protein, transcript variant b |
| C | ILMN_1683792 | LAP3 | Leucine aminopeptidase 3 |
| C | ILMN_1691731 | PARP14 | Poly (ADP-ribose) polymerase family, member 14 |
| C | ILMN_1751079 | TAP1 | Transporter 1, ATP-binding cassette, sub-family B (MDR/TAP) |
| C | ILMN_1765258 | HLA-E | Major histocompatibility complex, class I, E |
| C | ILMN_1767006 | PSMB8 | Proteasome (prosome, macropain) subunit, beta type, 8 (large multifunctional peptidase 7), transcript variant B |
| C | ILMN_1774287 | CFB | Complement factor B |
| C | ILMN_1779252 | TRIM22 | Tripartite motif-containing 22 |
| C | ILMN_1810910 | CFH | Complement factor H, transcript variant 2 |
| C | ILMN_2085862 | SLC15A3 | Solute carrier family 15, member 3 |
| C | ILMN_2170814 | LAMP3 | Lysosomal-associated membrane protein 3 |
| C | ILMN_2326509 | CASP1 | Caspase 1, apoptosis-related cysteine peptidase (Interleukin 1, beta, convertase), transcript variant delta |
| C | ILMN_2326512 | CASP1 | Caspase 1, apoptosis-related cysteine peptidase (Interleukin 1, beta, convertase), transcript variant delta |
| C | ILMN_2376108 | PSMB9 | Proteasome (prosome, macropain) subunit, beta type, 9 (large multifunctional peptidase 2), transcript variant 1 |
| C | ILMN_2412192 | CFH | Complement factor H, transcript variant 2 |
| D | ILMN_1654639 | HERC6 | Hect domain and RLD 6 |
| D | ILMN_1659688 | LGALS3BP | Lectin, galactoside-binding, soluble, 3 binding protein |
| D | ILMN_1659913 | ISG20 | Interferon stimulated exonuclease gene 20 kDa |
| D | ILMN_1661577 | MAFA | v-maf musculoaponeurotic fibrosarcoma oncogene homolog A (avian) |
| D | ILMN_1662358 | MX1 | Myxovirus (influenza virus) resistance 1, interferon-inducible protein p78 (mouse) |
| D | ILMN_1664543 | IFIT3 | Interferon-induced protein with tetratricopeptide repeats 3 |
| D | ILMN_1672661 | SP110 | SP110 nuclear body protein, transcript variant b |
| D | ILMN_1674811 | OASL | 2'-5'-oligoadenylate synthetase-like, transcript variant 2 |
| D | ILMN_1718558 | PARP12 | Poly (ADP-ribose) polymerase family, member 12 |
| D | ILMN_1742618 | XAF1 | XIAP associated factor 1, transcript variant 2 |
| D | ILMN_1745242 | PLSCR1 | Phospholipid scramblase 1 |
| D | ILMN_1776723 | PHF11 | PHD finger protein 11, transcript variant 1 |
| D | ILMN_1781373 | IFIH1 | Interferon induced with helicase C domain 1 |
| D | ILMN_1795181 | DDX60 | DEAD (Asp-Glu-Ala-Asp) box polypeptide 60 |

TABLE 1-continued

Lists of IFNα and IFNγ-responsive transcripts presented in FIG. 2

| Group | probe ID | Gene Symbol | Description |
|---|---|---|---|
| D | ILMN_1797001 | DDX58 | DEAD (Asp-Glu-Ala-Asp) box polypeptide 58 |
| D | ILMN_1799467 | SAMD9L | Sterile alpha motif domain containing 9-like |
| D | ILMN_1814305 | SAMD9 | Sterile alpha motif domain containing 9 |
| D | ILMN_2248970 | OAS2 | 2'-5'-oligoadenylate synthetase 2, 69/71 kDa, transcript variant 3 |
| D | ILMN_2262044 | PARP10 | Poly (ADP-ribose) polymerase family, member 10 |
| D | ILMN_2390162 | PHF11 | PHD finger protein 11, transcript variant 1 |
| E | ILMN_1670305 | SERPING1 | Serpin peptidase inhibitor, clade G (C1 inhibitor), member 1, transcript variant 2 |
| E | ILMN_1689655 | HLA-DRA | Major histocompatibility complex, class II, DR alpha |
| E | ILMN_1695311 | HLA-DMA | Major histocompatibility complex, class II, DM alpha |
| E | ILMN_1715169 | HLA-DRB1 | Major histocompatibility complex, class II, DR beta 1 |
| E | ILMN_1736567 | CD74 | CD74 molecule, major histocompatibility complex, class II invariant chain, transcript variant 1 |
| E | ILMN_1761733 | HLA-DMB | Major histocompatibility complex, class II, DM beta |
| E | ILMN_1772218 | HLA-DPA1 | Major histocompatibility complex, class II, DP alpha 1 |
| E | ILMN_1778010 | IL32 | Interleukin 32, transcript variant 7 |
| E | ILMN_1782487 | LOC400759 | Similar to Interferon-induced guanylate-binding protein 1 on chromosome 1 |
| E | ILMN_2114568 | GBP5 | Guanylate binding protein 5 |
| E | ILMN_2157441 | HLA-DRA | Major histocompatibility complex, class II, DR alpha |
| E | ILMN_2368530 | IL32 | Interleukin 32, transcript variant 4 |
| F | ILMN_1656310 | INDO | Indoleamine-pyrrole 2,3 dioxygenase |
| F | ILMN_1678841 | UBD | Ubiquitin D |
| F | ILMN_1701114 | GBP1 | Guanylate binding protein 1, interferon-inducible, 67 kDa |
| F | ILMN_1701613 | RARRES3 | Retinoic acid receptor responder (tazarotene induced) 3 |
| F | ILMN_1708375 | IRF1 | Interferon regulatory factor 1 |
| F | ILMN_1727271 | WARS | Tryptophanyl-tRNA synthetase, transcript variant 2 |
| F | ILMN_1774077 | GBP2 | Guanylate binding protein 2, Interferon-inducible |
| F | ILMN_1791759 | CXCL10 | Chemokine (C13 X—C motif) ligand 10 |
| F | ILMN_2148785 | GBP1 | Guanylate binding protein 1, Interferon-inducible, 67 kDa |
| F | ILMN_2334296 | IL18BP | Interleukin 18 binding protein, transcript variant A |
| F | ILMN_2337655 | WARS | Tryptophanyl-tRNA synthetase, transcript variant 1 |

Example 3

Figure 3:
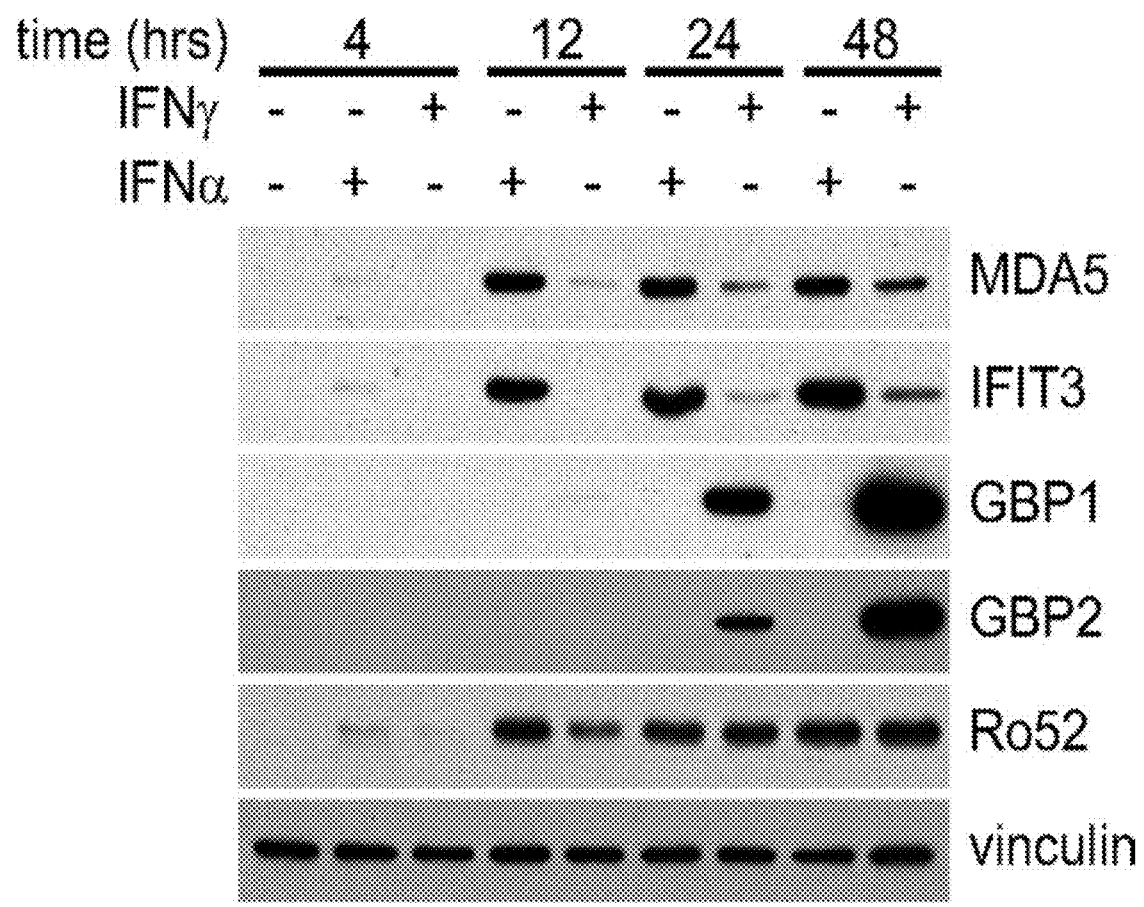
FIG. 3 is a Western blot validating probes of IFN-α and IFN-γ activity. Equivalent amounts of protein lysates from HSGs cultured for 4, 12, 24, or 48 hours in the absence or presence of IFN-α (1,000 U/mL) or IFN-γ (50 ng/mL) were analyzed by Western blotting. Antibodies against IFN-α-specific, IFN-γ-specific, and IFN-α/γ-responsive molecules as defined by array were used. Vinculin is included as a loading control.

Biochemical Validation of Probes of IFN Activity. We next sought to confirm these patterns at the level of protein expression. HSGs were treated with IFN-α or IFN-γ for 4, 12, 24, or 48 hours and immunoblotted equivalent amounts of protein lysates. Antibodies recognizing several IFN-α and IFN-γ-preferential genes were tested to select the highest quality probes for use in differentiating between IFN-α and IFN-γ activity in human tissues (FIG. 3). Several observations were relevant: (i) IFN-inducible proteins were not detectable in untreated cells; (ii) as defined in the optimization phase, Ro52 was induced to equivalent levels by IFN-α and IFN-γ at 24 and 48 hours; (iii) the IFN-α response was rapid, with maximal expression of MDA5, IFIT3, and Ro52 detected at 12 hours; this remained elevated through 48 hours; (iv) the IFN-γ response occurred more slowly, with protein expression peaking at 48 hours; (v) MDA5 and IFIT3 were IFN-α specific at 12 hours but were IFN-γ responsive (albeit at markedly lower levels than the IFN-α response) at 24 and 48 hours; (vi) GBP1 and GBP2 were robustly and specifically induced by IFN-γ only; (vii) a low dose of IFN-γ enhanced the expression of MDA5 and IFIT3 in IFN-α-treated cells, whereas IFN-α did not enhance the induction of GBP1 and GBP2 (not shown). Quantifying the expression of IFN-γ-specific proteins (e.g., GBP1, GBP2) in human tissues is therefore necessary to accurately differentiate between IFN-α and IFN-γ activity in vivo.

Example 4

Figure 4:
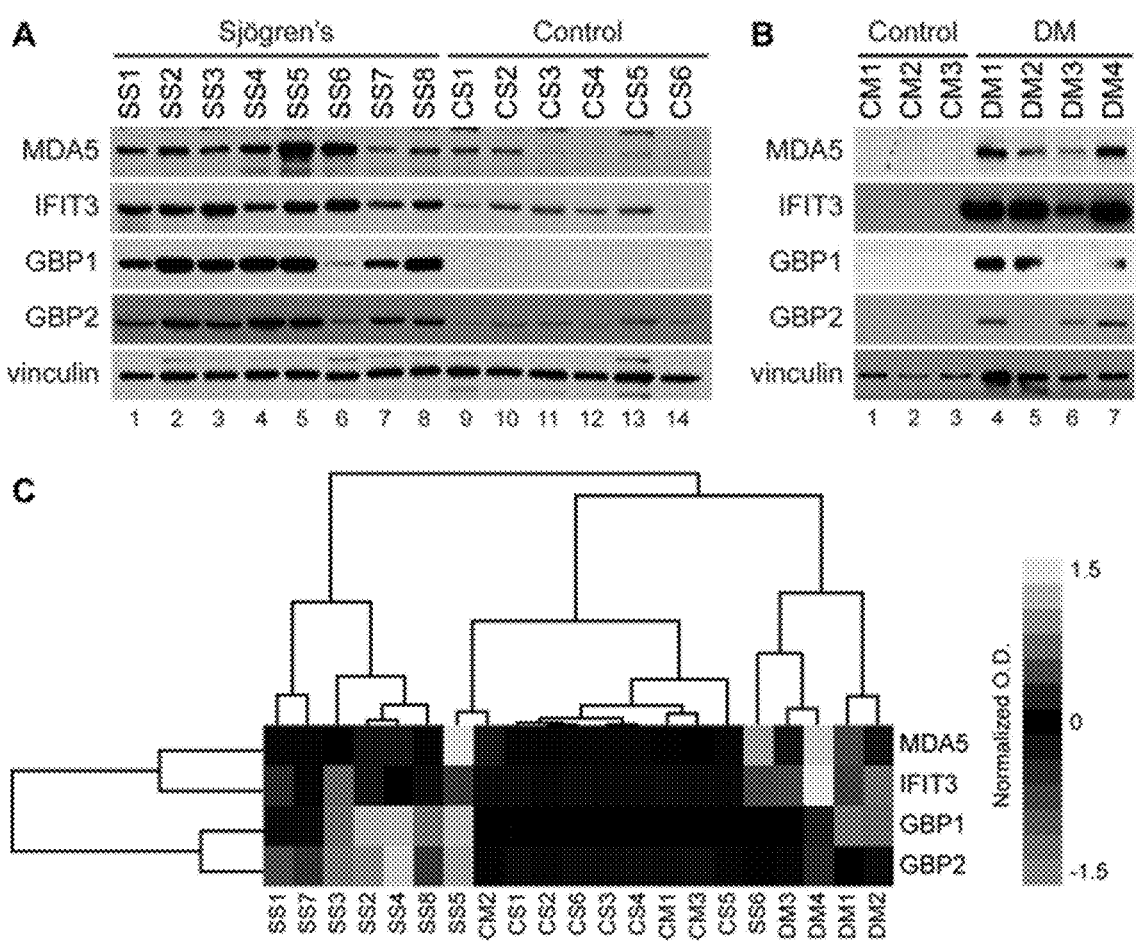
FIG. 4 shows distinct patterns of type I and type II IFN-induced proteins in SS and DM tissue biopsies. (A) Protein lysates made from control (CS, n=6) and SS (SS, n=8), MSG biopsies were probed for IFN-inducible protein expression by Western blotting. Markers of type I IFN (MDA5, IFIT3) and type II IFN (GBP1, GBP2) were analyzed. Vinculin is included as a loading control. (B) Protein lysates made from control (CM, n=3) and DM (DM, n=4) muscle biopsies were probed with markers of type I and type II IFN. Vinculin is included as a loading control. (C) IFN-induced protein expression from A and B was quantified by densitometry and normalized to the level of vinculin expression in the respective sample. Vinculin-normalized expression values were median centered and subject to unsupervised hierarchical clustering to define patterns of IFN-induced protein expression in individual patients.

Type I and Type II IFN Activity Is Prominent in Minor Salivary Gland Biopsies from SS Patients. To define the IFN pathways represented in SS, protein expression was analyzed in lysates of minor salivary gland biopsies from SS patients (n=8) and controls (n=6). These samples were immunoblotted with antibodies against IFIT3, MDA5, GBP1, GBP2, and vinculin (loading control). Although IFN-induced protein expression was generally low or absent in control salivary glands, some heterogeneity was noted, particularly for MDA5 and IFIT3, which likely reflects variability in baseline expression levels. In SS, striking increases in the expression of MDA5, IFIT3, GBP1, and GBP2 were evident in most patients, indicating both type I and type II IFN effects in most biopsies (FIG. 4A). Although six of eight patients had elevated expression of both IFN-α- and IFN-γ-induced proteins, there was some variation in patterns between individual patients, with one patient exhibiting a predominantly IFN-α pattern (FIG. 4A, lane 6) and one demonstrating a predominantly IFN-γ pattern (FIG. 4A, lane 7).

Example 5

To define whether markers of both type I and type II IFNs were similarly present in tissues from another autoimmune rheumatic disease in which an IFN signature is prominent, muscle tissue from patients with DM was analyzed. Expression of the panel of IFN-induced molecules was examined in control (n=3) and DM (n=4) muscle biopsy lysates by immunoblotting (FIG. 4B). IFN-inducible proteins were not detected in control muscle. In contrast to SS tissues, there was marked expression of IFIT3 in DM muscle with comparably lower expression of GBP1 and GBP2, suggestive of a type I IFN response in these samples. To compare the patterns in SS and DM, the data were quantified by densitometry and the expression levels of IFIT3, MDA5, GBP1, and GBP2 were normalized to the expression level of a loading control, vinculin, in each sample. The normalized data were subjected to unsupervised hierarchical clustering to define subgroups (FIG. 4C). Interestingly, the IFN-α-preferential markers and the IFN-γ-specific markers clustered separately. With a single exception (SS6), SS patients were clearly separated from controls and from DM patients. SS6 had a predominant type I IFN pattern, and was more similar to DM than either SS or controls.

Example 6

Figure 5:
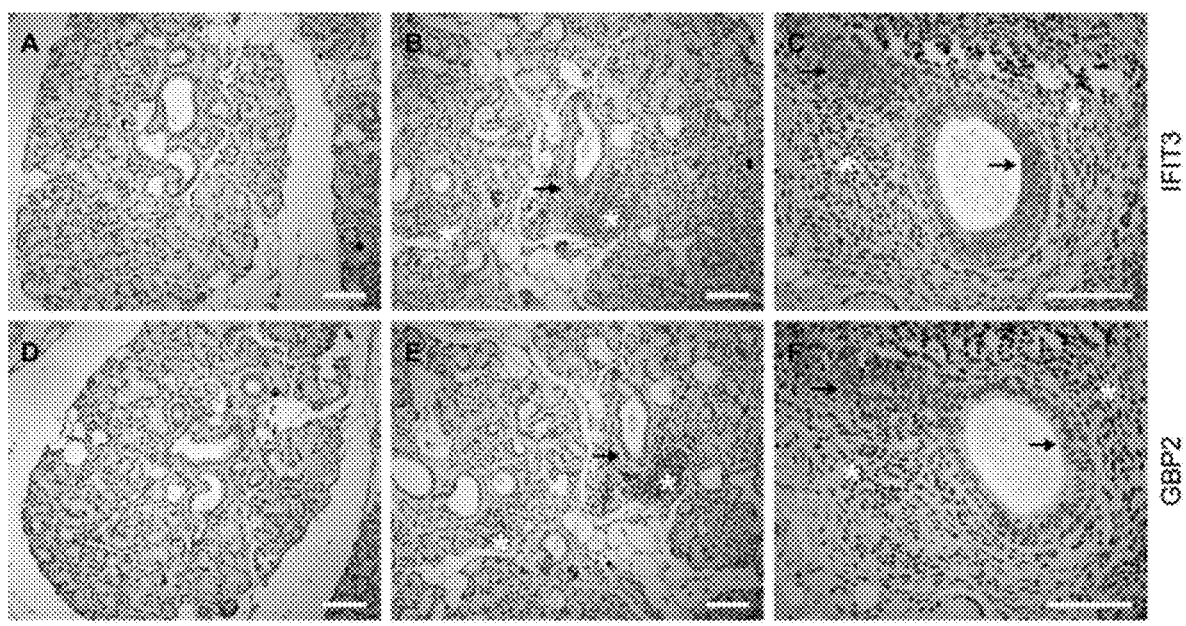
FIG. 5 depicts colocalization of markers of type I and type II IFN activity in SS salivary gland biopsies. Minor salivary gland biopsies from controls (n=3) and patients with SS (n=4) were stained with antibodies against the type I IFN-preferential protein IFIT3 (A-C) and the IFN-γ-specific protein GBP2 (D-F). Representative images from one control (A and D) and two SS (B, C, E, and F) biopsies are shown. Staining with isotype control antibodies was negative in all samples (data not shown). The asterisks denote areas of inflammation, and the arrows designate salivary gland epithelial cells that express both IFIT3 and GBP2. (Scale bars, 50 μm.)
Figure 6:
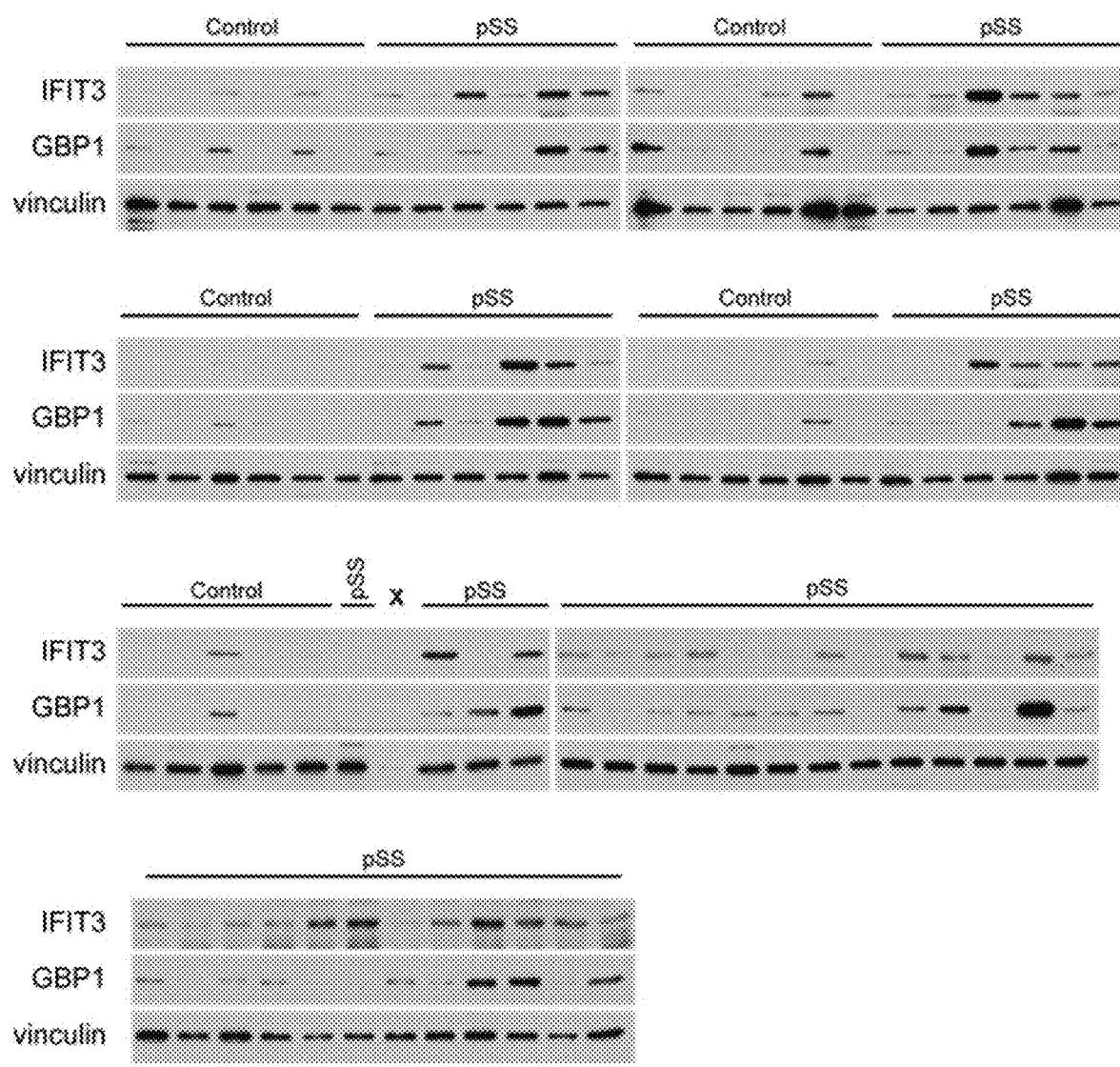
FIG. 6 depicts distinct patterns of IFN activity in minor salivary gland biopsies from SS patients. Protein lysates made from control (Control, n=29) and SS (pSS, n=53), minor salivary gland biopsies were probed for IFN-inducible protein expression by Western blotting. Markers of type I IFN (IFIT3) and type II IFN (GBP1) were analyzed. Vinculin is included as a loading control.
Figure 7:
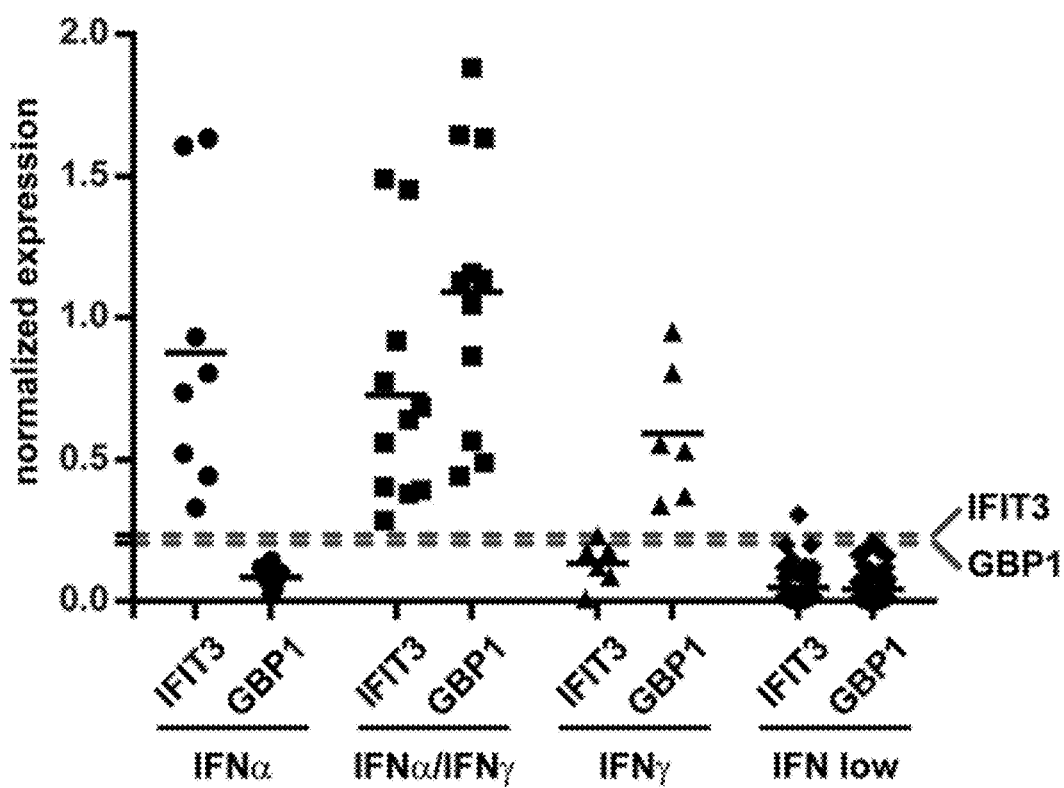
FIG. 7 depicts vinculin-normalized IFIT3 and GBP1 expression values for SS patients and controls used for establishing a cutoff for a positive value. Vinculin-normalized IFIT3 and GBP1 expression from 53 SS patients and 29 controls was subject to unsupervised heirarchical clustering. 4 distinct groups were identified based on predominant IFN pathway activity: IFN-α (n=8)—circles; IFN-α and IFN-γ (n=11)—squares; IFN-γ (n=6)—triangles; and IFN low/null (n=57)—diamonds. Vinculin-normalized expression values are indicated on the Y-axis. The mean expression levels in each group are indicated (bars). Dotted lines indicate 3 S.D. from the mean expression levels of the IFN low group.

Evidence of both Type I and II IFN Activity in Salivary Gland Epithelial Cells. We next defined the cells in SS salivary glands that express markers of type I and type II IFN effects by immunohistochemistry. Serial sections of four SS and three control salivary glands were stained, and representative data from two SS patients are shown in FIG. 5. Minimal IFIT3 and GBP2 staining was seen in control salivary glands (FIGS. 5 A and D). Expression of IFIT3 and GBP2 was increased in SS salivary gland biopsies, consistent with the biochemical studies. The predominant staining pattern showed IFIT3 expression mainly in salivary duct epithelial cells, particularly in regions surrounded by inflammatory cells (FIGS. 5 B and C). Minimal IFIT3 staining was observed in infiltrating inflammatory cells. In contrast, GBP2 was prominently expressed in the nuclei of infiltrating inflammatory cells. GBP2 staining was also evident in salivary ducts, where the nuclei of both infiltrating inflammatory cells (strong staining) as well as duct epithelium were stained (moderate staining). Interestingly, GBP2 and IFIT3 stained the same regions of the ducts that were surrounded by GBP2-positive inflammatory cells (FIGS. 5 E and F). Isotype control antibody staining was negative for all samples (data not shown).

Example 7

IFN pathway analysis in control and SS minor salivary gland biopsies. Equivalent amounts of protein lysates from 29 control (Cont) and 53 SS (pSS) patient minor salivary gland biopsies were analyzed for IFN-inducible protein expression by Western blotting. IFIT3 was utilized to report of the activity of IFN-α and GBP1 was utilized to report on the activity of IFN-γ. Vinculin is included as a loading control.

Example 8

Distinct patterns of IFN pathway activity are evident in minor salivary gland biopsies from SS patients. Vinculin-normalized IFIT3 and GBP1 expression from 53 SS patients and 29 controls was subject to unsupervised heirarchical clustering. 4 distinct groups were identified based on predominant IFN pathway activity: IFN-α (n=8)—circles; IFN-α and IFN-γ (n=11)—squares; IFN-γ (n=6)—triangles; and IFN low/null (n=57)—diamonds. Vinculin-normalized expression values are indicated on the Y-axis. The mean expression levels in each group are indicated (bars). Dotted lines indicate 3 S.D. from the mean expression levels of the IFN low group.

Although the presence of IFN signatures in the target tissue in rheumatic diseases has been well defined, there has not been an opportunity to simultaneously visualize the activity of IFN-α and IFN-γ by immunohistochemistry in the same tissues. The present inventive methods demonstrate some interesting findings in this regard. First, expression of IFIT3 and GBP2 was enriched in the same areas of SS salivary glands. Second, IFIT3 and GBP2 were both expressed in salivary epithelial cells located in areas of significant inflammatory infiltrate, although the patterns differed. IFIT3 staining was enriched in ductal epithelial cells and did not stain inflammatory cells with similar intensity. In contrast, although GBP2 expression in ductal epithelial cells in inflamed areas was clearly evident, expression of GBP2 was more prominent in surrounding infiltrating mononuclear cells. These patterns demonstrate that epithelial cells in areas of inflammation in the SS glands are showing the effects of both types of IFNs. This localized distribution suggests that the type I and type II IFN pathways converge in epithelial cells at these sites. Because small amounts of type II IFN can enhance IFIT3 expression (data not shown) induced by type I IFN, it is possible that the striking IFIT3 staining in SS epithelium reflects the sensitizing effects of local IFN-γ. It is also possible that the ability of IFN-γ to enhance signaling through Toll-like receptors (TLRs) (e.g., TLR3), with augmentation of type I IFN secretion and downstream pathways, may enhance the type I IFN effect in the presence of relevant TLR ligands. It is noteworthy that some of the prominent ribonucleoprotein autoantigens targeted in autoimmune rheumatic diseases like SS can ligate and activate TLRs. The existence of positively reinforcing interactions between the different IFN pathways in SS may provide important therapeutic opportunities. Quantifying IFIT3 and GBP2 expression in the target tissue during therapy with inhibitors of specific IFN pathways provides important tools for investigating the nature and direction of these reinforcing interactions.

The present inventive methods have defined probes that more precisely quantify the activity of different IFN pathways in tissues from various inflammatory rheumatic diseases. Using these inventive probes on human tissue has demonstrated that different rheumatic phenotypes associated with an IFN signature have distinct patterns of IFN activity, which are not evident using other analyses. Furthermore, heterogeneity in signatures exists even within a disease phenotype, which means that the probes provided herein are be useful markers of patient subsets, where specific IFNs play distinct roles. As new therapeutic agents that inhibit type I or type II IFNs become available, it will be essential to identify with precision the activity of that pathway in vivo at baseline and after therapy. The inventive methods and tools defined here can be used to accomplish this.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for establishing the IFN expression profile of a salivary gland and/or muscle tissue from an autoimmune rheumatic disease patient comprising:
   a) preparing a salivary gland and/or muscle tissue sample of the autoimmune rheumatic disease patient; and
   b) analyzing the prepared tissue sample of a) for the presence of both markers of type I IFN activity selected from the group consisting of MDA5 and IFIT3, and two or more markers of type II IFN activity selected from the group consisting of: GBP1, GBP2, INDO, UBD, RARRES3, CXCL10, IL18BP, SERPING1, and GBP5, by quantification of protein expression using an immunohistochemical method.

2. The method of claim 1, wherein the autoimmune rheumatic disease patient has Sjögren syndrome (SS), dermatomyositis (DM), polymyositis, scleroderma, or systemic lupus erythematosus (SLE).

3. The method of claim 1, wherein step b) comprises analyzing the prepared tissue sample of a) for the presence of both markers of type I IFN activity selected from the group consisting of MDA5 and IFIT3, and three or more markers of type II IFN activity selected from the group consisting of: GBP1, GBP2, INDO, UBD, RARRES3, CXCL10, IL18BP, SERPING1, and GBP5.

4. The method of claim 1, wherein step b) comprises analyzing the prepared tissue sample of a) for the presence of both markers of type I IFN activity selected from the group consisting of MDA5 and IFIT3, and four or more markers of type II IFN activity selected from the group consisting of: GBP1, GBP2, INDO, UBD, RARRES3, CXCL10, IL18BP, SERPING1, and GBP5.

5. The method of claim 1, wherein step b) comprises analyzing the prepared tissue sample of a) for the presence of both markers of type I IFN activity selected from the group consisting of MDA5 and IFIT3, and five or more markers of type II IFN activity selected from the group consisting of: GBP1, GBP2, INDO, UBD, RARRES3, CXCL10, IL18BP, SERPING1, and GBP5.

6. The method of claim 1, wherein step b) comprises analyzing the prepared tissue sample of a) for the presence of both markers of type I IFN activity selected from the group consisting of MDA5 and IFIT3, and markers of type II IFN activity selected from the group consisting of GBP1 and GBP2.

7. The method of claim 1, wherein step b) comprises analyzing the prepared tissue sample of a) for the presence of both markers of type I IFN activity selected from the group consisting of MDA5 and IFIT3, and markers of type II IFN activity selected from the group consisting of GBP1, GBP2, and UBD.

8. The method of claim 1, wherein step b) comprises analyzing the prepared tissue sample of a) for the presence of both markers of type I IFN activity selected from the group consisting of MDA5 and IFIT3, and markers of type II IFN activity selected from the group consisting of GBP1, GBP2, and CXCL10.

9. The method of claim 1, wherein step b) comprises analyzing the prepared tissue sample of a) for the presence of both markers of type I IFN activity selected from the group consisting of MDA5 and IFIT3, and markers of type II IFN activity consisting of GBP1, GBP2, and one or more markers selected from the group consisting of INDO, UBD, RARRES3, CXCL10, IL18BP, SERPING1, and GBP5.

* * * * *

UNITED STATES PATENT AND TRADEMARK OFFICE
CERTIFICATE OF CORRECTION

| | |
|---|---|
| PATENT NO. | : 11,366,113 B2 |
| APPLICATION NO. | : 15/973688 |
| DATED | : June 21, 2022 |
| INVENTOR(S) | : John Clayton Hall, Livia Casciola-Rosen and Antony Rosen |

It is certified that error appears in the above-identified patent and that said Letters Patent is hereby corrected as shown below:

In the Specification

- In Column 1, Line 8, please delete "Nov. 17, 2015" and insert -- Nov. 17, 2014 --.

Signed and Sealed this
Eighteenth Day of April, 2023

Katherine Kelly Vidal
*Director of the United States Patent and Trademark Office*